US00PP36759P2

(12) United States Plant Patent
Schoemaker

(10) Patent No.: US PP36,759 P2
(45) Date of Patent: Jun. 24, 2025

(54) ***HYDRANGEA* PLANT NAMED 'LC NO22'**

(50) Latin Name: *Hydrangea arborescens*
Varietal Denomination: LC NO22

(71) Applicant: Alex Shoemaker Living Creations Holding B.V., Boskoop (NL)

(72) Inventor: Alex F. Schoemaker, Boskoop (NL)

(73) Assignee: Alex Schoemaker Living Creations Holding B.V. (NL)

( * ) Notice: Subject to any disclaimer, the term of this patent is extended or adjusted under 35 U.S.C. 154(b) by 0 days.

(21) Appl. No.: 18/950,515

(22) Filed: Nov. 18, 2024

(51) Int. Cl.
*A01H 5/00* (2018.01)
*A01H 6/48* (2018.01)

(52) U.S. Cl.
USPC ..... Plt./250
CPC ..... *A01H 6/48* (2018.05)

(58) Field of Classification Search
USPC ..... Plt./250
CPC ..... A01H 5/00
See application file for complete search history.

*Primary Examiner* — Kent L Bell
(74) *Attorney, Agent, or Firm* — Cassandra Bright

(57) ABSTRACT

A new and distinct cultivar of *Hydrangea arborescens* plant named 'LC NO22' is disclosed, characterized by sturdy stems on medium sized, compact plants. Plants are highly floriferous and flower from June to September. The sterile flowers have ornamental sepals that are red-purple from the beginning to the end of the flower period. The new variety is a *Hydrangea*, typically produced as an outdoor ornamental plant.

3 Drawing Sheets

Latin name of the genus and species: *Hydrangea arborescens*.

Cultivar denomination: 'LC NO22'.

BACKGROUND OF THE INVENTION

The new cultivar is a product of a planned breeding program conducted by the inventor in Boskoop, the Netherlands. The inventor crossed two unnamed, unpatented proprietary seedlings in 2014. The new cultivar 'LC NO22' was selected by the inventor in 2019 from seedlings developed from the 2014 crossing.

Asexual reproduction of the new cultivar 'LC NO22' was first performed during summer of 2019 in in Boskoop, the Netherlands, by softwood cuttings. Through subsequent propagation, multiple additional generations have been reproduced, having shown that the unique features of this cultivar are stable and reproduced true to type.

The inventor has filed an application with the CPVO Nov. 21, 2023, having application number 2023/2431. This disclosure falls within the exception allowed under 102(b)(1).

SUMMARY OF THE INVENTION

The cultivar 'LC NO22' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'LC NO22'. These characteristics in combination distinguish 'LC NO22' as a new and distinct *Hydrangea* cultivar:

1. Sturdy stems.
2. Medium, compact plant size.
3. Highly floriferous plants.

4. Red-Purple sepals retaining color from the beginning to the end of the flowering period.
5. Flowering period from June to September.

PARENT COMPARISON

Plants of 'LC NO22' are similar to plants of both parents in most horticultural characteristics, however, plants of 'LC NO22' differ in the following:

1. Plants of the new cultivar have a longer flowering period than plants of either parent.
2. Foliage of the new cultivar is darker green than foliage of either parent.

COMMERCIAL COMPARISONS

Plants of 'LC NO22' can be compared to plants of the commercial cultivar *Hydrangea arborescens* 'GRHYAR1406', U.S. Plant Pat. No. 31,121. Plants of 'LC NO22' are similar to plants of 'GRHYAR1406' in most horticultural characteristics, however, plants of 'LC NO22' differ in the following:

1. 'LC NO22' has darker pink sterile flower sepals than 'GRHYAR1406'.

Plants of the new cultivar *Hydrangea* 'LC NO22' can be compared to the commercial cultivar *Hydrangea arborescens* 'Hyso22', unpatented. Plants of 'LC NO22' are similar to plants of 'Hyso22' in most horticultural characteristics, however, plants of 'LC NO22' differ in the following:

1. Panicles of the new cultivar are larger than panicles of this comparator.
2. 'LC NO22' has darker pink sterile flower sepals than this comparator.

BRIEF DESCRIPTION OF THE PHOTOGRAPHS

The accompanying photograph in FIG. 1 illustrates in full color a typical plant of 'LC NO22' grown in a field in Boskoop, the Netherlands. This plant is approximately 3 years old, grown in the ground, photographed in the middle of July.

Figure 1:
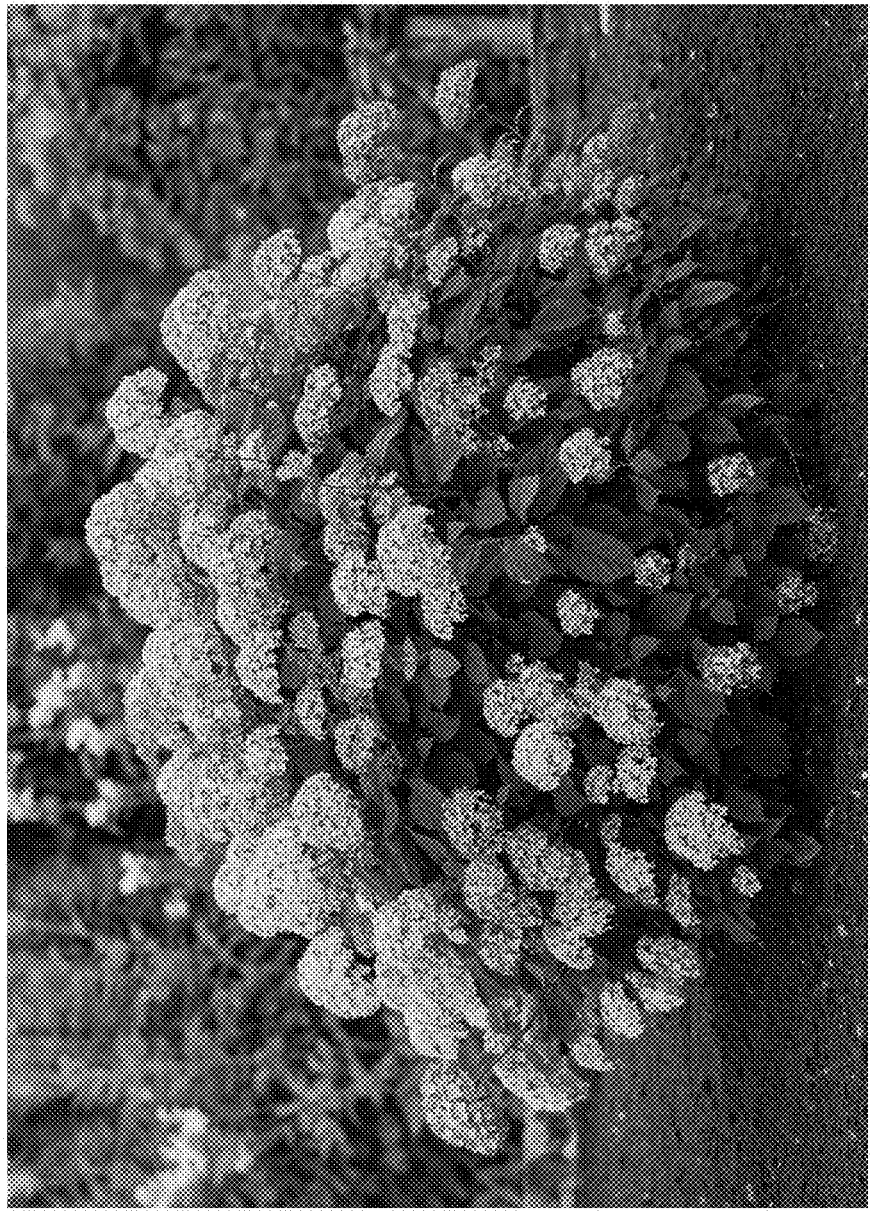
Figure 2:
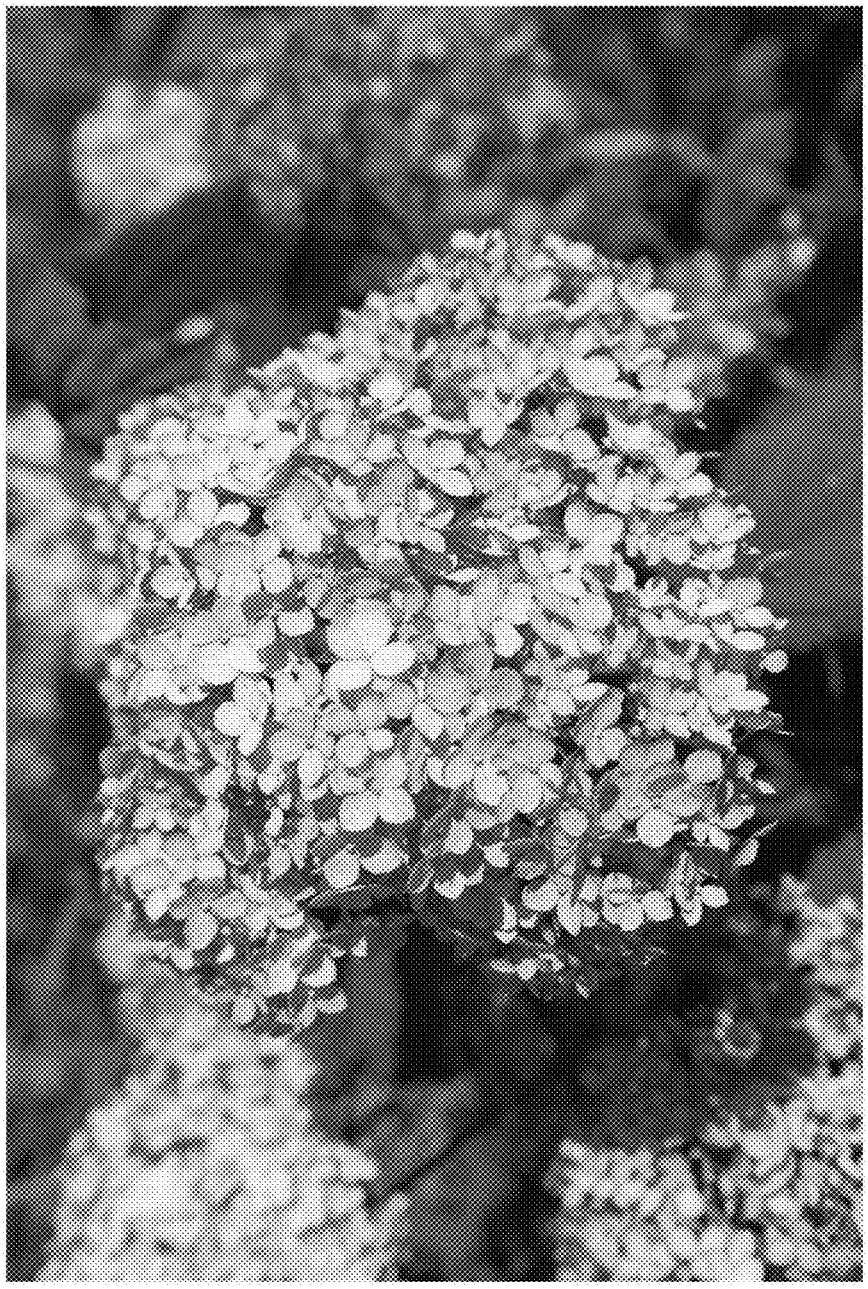
FIG. 2 illustrates in full color a close-up view of typical inflorescences of 'LC NO22' during June, having typical early summer sepal coloration.
Figure 3:
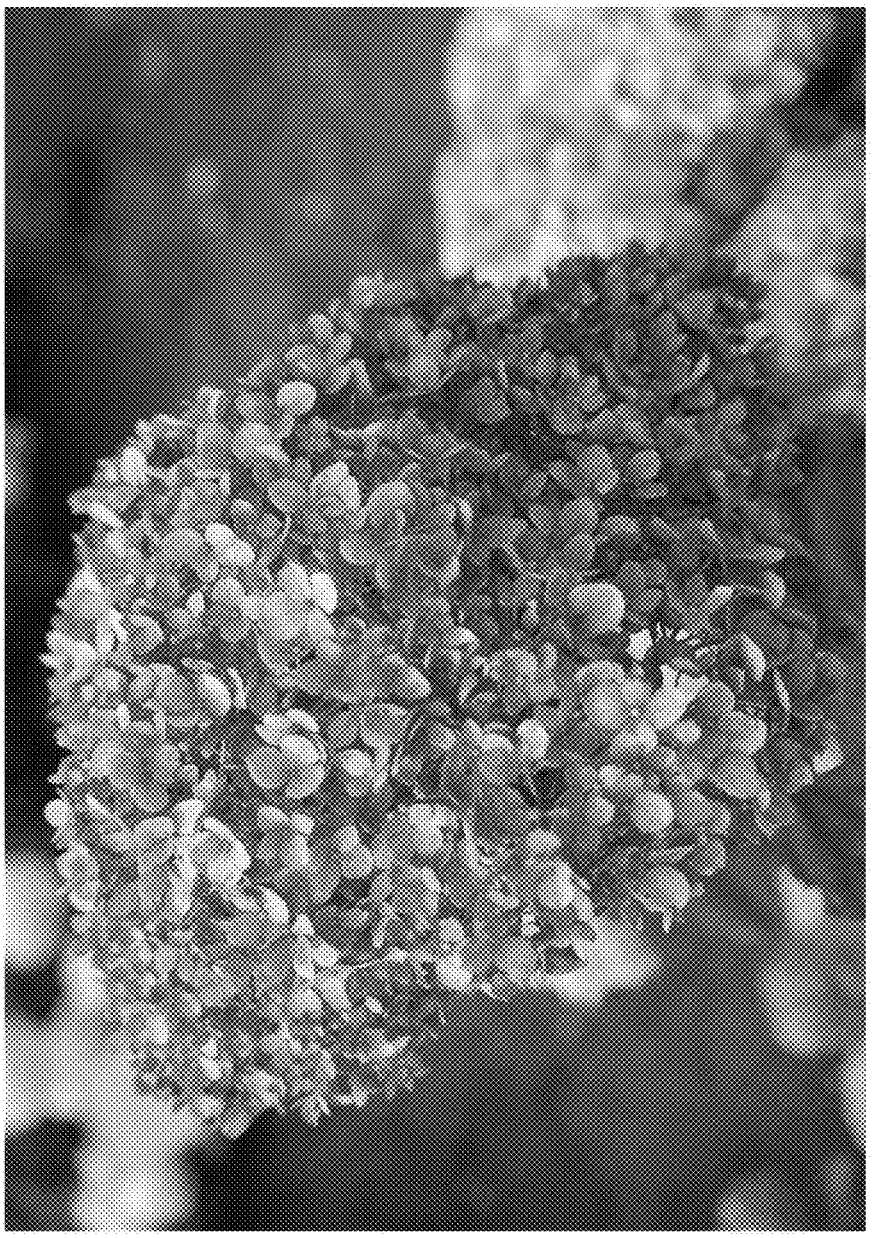
FIG. 3 is a close-up view of a typical panicle of 'LC NO22' during July, having the deeper coloration typical of the sepals later in Summer.

The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2015, except where general terms of ordinary dictionary significance are used. The following observations and measurements describe 'LC NO22' plants grown outdoors in Boskoop, the Netherlands. The plants were about 3-years old. Temperatures ranged from about 5° C. to 10° C. at night to 18° C. to 27° C. during the day. No artificial light, photoperiodic treatments were given to the plants. Measurements and numerical values represent averages of typical plant types.

Botanical classification: *Hydrangea arborescens* 'LC NO22'.

PROPAGATION

Typical method: Softwood cuttings.

Roots: Thin, freely branching, fibrous, moderately dense. Yellow-white in color, not accurately measured with R.H.S. chart.

PLANT

Growth habit: Compact and semi-upright. Deciduous flowering shrub.

Shape: Rounded.

Height: 80 to 100 cm.

Plant spread: 150 cm.

Plant vigor: High vigor.

Stem:

- *Branching*.—Basal, freely.
- *Number of branches*.—About 30.
- *Shape*.—Round.
- *Color*.—Immature: RHS Yellow-Green 144B and 144C. Mature: RHS Grey-Brown N199A and N199B.
- *Length*.—100 cm.
- *Width*.—10 mm.
- *Strength*.—Very strong.
- *Texture*.—Glabrous.
- *Internode length*.—10 cm.

FOLIAGE

Leaf:

- *Arrangement*.—Opposite.
- *Shape*.—Broad obovate.
- *Length*.—12 cm.
- *Width*.—10 cm.
- *Apex*.—Acute to acuminate.
- *Base*.—Rounded.
- *Margin*.—Moderately serrate.
- *Texture of top surface*.—Slightly pubescent.
- *Texture of bottom surface*.—Slightly pubescent.
- *Color*.—Young Foliage, Upper Side: RHS Yellow-Green 144B and 144C. Young Foliage, Under Side: RHS Yellow-Green 144D. Mature Foliage, Upper Side: RHS Yellow-Green 137A. Mature Foliage, Under Side: RHS Yellow-Green 144C.

Venation:

- *Type*.—Pinnate.
- *Color*.—Mature, Upper Side: RHS Yellow-Green 144C and 144D. Mature, Under Side: RHS Yellow-Green 144D.

Petiole:

- *Length*.—8 cm.
- *Width*.—3 to 4 mm.
- *Color*.—Upper Side: RHS Greyed-Purple 183A. Under Side: RHS Yellow-Green 145A.
- Texture.—Upper Side: Lightly pubescent. Under Side: Lightly pubescent.

INFLORESCENCE

Natural flowering season: June to September.

Inflorescence type: Mophead.

Lastingness: About 8 weeks.

Conspicuousness of fertile flowers: Absent.

Panicle:

- *Shape*.—Globular.
- *Height*.—13 cm.
- *Diameter*.—20 cm.

Fragrance: None.

Sterile flowers:

- *Flowers per inflorescence*.—200 to 300.
- *Aspect*.—Upright.
- *Shape*.—Rotate.
- *Length*.—2 cm.
- *Diameter*.—2 cm.
- *Persistence*.—Persistent.

Bud:

- *Length*.—1 mm.
- *Diameter*.—1 mm.
- *Shape*.—Globular.
- *Color*.—Emerging Yellow-Green 144C, turning Greyed-Orange 175A and Greyed-Purple 183A.

Petals: 4 petals, each 1 mm in width and length. Orbicular in shape, glabrous texture. Apex obtuse, base obtuse, margin entire, colored same as the sepals.

Sepals:

- *Number*.—3 or 4.
- *Arrangement*.—Rotate.
- *Shape*.—Ovate.
- *Tip*.—Acute.
- *Base*.—Obtuse.
- *Margin*.—Entire.
- *Length*.—9 mm.
- *Width*.—6 mm.
- *Texture*.—Upper side: Glabrous. Under side: Glabrous.
- *Color*.—When Opening, Upper Side: RHS Yellow-Green 145D streaked Red-Purple 59C and 58D. When Opening, Under Side: RHS Red-Purple 59B and 59C. Fully First Opened early Summer, Upper Side: RHS Red-Purple 59D streaked 58D. Margins and veins 59C. Fully First Opened early Summer, Under Side: RHS Red-Purple 59C. Fully Opened late Summer, Upper Side: RHS Red-Purple 62D streaked 62C. Margins and veins 59C and 59D. Fully Opened late Summer, Under Side: RHS Red-Purple 63D streaked 58C. Margins and veins 59C and 59D.

Pedicel:

*Length.*—1 to 2 cm.
*Diameter.*—1 mm.
*Strength.*—Moderately strong.
*Texture.*—Slightly pubescent.
*Color.*—RHS Yellow-Green 145D flushed Red-Purple 59C and 59D.

Fertile flowers:

*Flowers per inflorescence.*—100.
*Aspect.*—Upright.
*Shape.*—Whorl.
Length.—4 mm.
Diameter.—4 mm.

Bud:

*Length.*—1.5 mm.
*Diameter.*—1.5 mm.
*Bud shape.*—Globose.
*Bud color.*—RHS Yellow-Green 145D.

Sepals:

*Number per flower.*—5.
*Arrangement.*—Rotate.
*Shape.*—Elliptic.
*Tip.*—Acute.
*Base.*—Cuneate.
*Margin.*—Entire.
*Length.*—1 mm.
*Width.*—1 mm.
*Texture.*—Upper Side: Glabrous. Under Side: Glabrous.
*Color.*—Upper Side: RHS Yellow-Green 145D flushed Red-Purple 59C and 59D. Under Side: RHS Yellow-Green 145D flushed Red-Purple 59C and 59D.

Petals:

*Number per flower.*—5.
*Arrangement.*—Rotate.
*Shape.*—Ovate.
*Tip.*—Acute.
*Base.*—Truncate.
*Margin.*—Entire.
*Length.*—1.5 mm.
*Width.*—1.5 mm.
*Texture.*—Upper Side: Glabrous. Under Side: Glabrous.
*Color.*—Upper Side: RHS White N155B slightly flushed Red-Purple 59C and 59D. Under Side: RHS White N155B slightly flushed Red-Purple 59C and 59D.

Pedicel:

*Length.*—3 mm.
*Diameter.*—1 mm.
*Texture.*—Slightly pubescent.
*Color.*—RHS Yellow-Green 145D flushed Red-Purple 59D.

REPRODUCTIVE ORGANS

Sterile flower: Not observed.

Fertile flower:

Stamens:

*Number.*—9 to 10.
*Filament length.*—3 mm.
*Filament color.*—RHS White NN155D.

Anthers:

*Shape.*—Globose.
*Length.*—0.05 mm.
*Color.*—RHS White NN155D.
*Pollen amount.*—None observed.

Pistil:

*Number.*—2.
*Length.*—1 mm.

Stigma:

*Shape.*—Round.
*Color.*—RHS White NN155D.
*Style length.*—0.05 mm.
*Style color.*—RHS White NN155D.
*Ovary color.*—Indistinguishable.

SEEDS

Not observed.

OTHER CHARACTERISTICS

Disease resistance: Neither resistance nor susceptibility to the normal diseases and pests of *Hydrangea* has been observed.

Cold tolerance: Hardy to −15° C.

What is claimed is:

1. A new and distinct cultivar of *Hydrangea* plant named 'LC NO22' as herein illustrated and described.

* * * * *